United States Patent [19]

Ishikawa et al.

[11] Patent Number: 4,924,083

[45] Date of Patent: May 8, 1990

[54] METHOD AND DEVICE FOR INSPECTING SIDEWALL OF BOTTLE

[75] Inventors: Kazushi Ishikawa; Shinsaku Yamamoto, both of Yokohama; Hisao Katogi, Hino, all of Japan

[73] Assignee: Kirin Beer Kabushiki Kaisha, Tokyo, Japan

[21] Appl. No.: 336,792

[22] Filed: Apr. 12, 1989

[30] Foreign Application Priority Data

Apr. 13, 1988 [JP] Japan .................. 63-90888

[51] Int. Cl.$^5$ .............................................. G01N 9/04
[52] U.S. Cl. .................. 250/223 B; 356/240; 209/525
[58] Field of Search .................. 250/223 B; 356/240, 356/239; 209/524, 525, 526

[56] References Cited

U.S. PATENT DOCUMENTS

4,367,405  1/1983  Ford ................................. 209/526
4,399,357  8/1983  Dorf ................................. 209/526
4,655,349  4/1987  Joseph ............................ 250/223 B Primary Examiner—David C. Nelms
Assistant Examiner—Sherrie Hsia
Attorney, Agent, or Firm—Fleit, Jacobson, Cohn, Price, Holman & Stern

[57] ABSTRACT

A method and a device for inspecting the sidewall of a bottle is disclosed. In the method and device for inspecting the sidewall of the bottle, an elongate illumination portion is moved to irradiate illumination light to the sidewall of the bottle to be inspected, an elongate observation portion moved synchronously with the elongate illumination portion to observe the illumination light transmitted through the sidewall of the bottle, and based on an image of the transmitted light, the presence of defects is judged. Light blocking defects and refractional defects on the sidewall of the bottle can be detected with high precision.

12 Claims, 8 Drawing Sheets

METHOD AND DEVICE FOR INSPECTING SIDEWALL OF BOTTLE

BACKGROUND OF THE INVENTION

This invention relates to a method and a device for inspecting the sidewall of a bottle which detect defects on the sidewall of the bottle.

It is necessary to inspect glass bottles for liquors, beverages, foods, etc. which have been recovered for reuses or even those which are fresh from bottle forming devices. These bottles are inspected at portions, i.e., the bodies or sidewalls, bottoms, tops of the mouths, and threaded necks. Sidewalls tend to have defects of foreign matters, stains, etc. which involve food sanitary problems, and defects of checks, cracks scratches, seeds, and blisters Which may initiate breakages of the bottles. These defects have to be correctly detected so as to remove defective bottles. To this end there has been proposed a method for detecting these defects, based on a darkness distribution of an image formed by the transmitted light through a transparent or opaque bottle.

But this proposed method has a problem that a darkness distribution of a transmitted light image of the sidewall of a bottle is indicative of a light blocking defect of foreign matters, stains, etc., but is insufficient to indicate refractional defects of seeds, blisters, streaks, rumples, etc. Another problem of this method is that it is difficult to discriminate from a refractional defect a joint running lengthwise on the sidewall of a bottle which is formed inevitably when the bottle is formed.

SUMMARY OF THE INVENTION

An object of this invention is to provide a method and a device for inspecting the sidewall of a bottle which is capable of detecting with high precision not only light blocking defects but also refractional defects of the sidewall of &he bottle.

This object is achieved by a method for inspecting the sidewall of a bottle comprising the steps of moving an elongate illumination portion to irradiate illumination light to the entire sidewall of the bottle to be inspected; observing the illumination light transmitted through the sidewall of the bottle by an elongate observation portion moved synchronously with the illumination portion to observe an image of the entire sidewall formed by the transmitted light; and judging whether there is a defect on the sidewall of the bottle, based on the transmitted light image.

This object is also achieved by a device for inspecting the sidewall of a bottle comprising: an illumination unit for moving an elongate illumination portion to irradiate illumination light to the entire sidewall of the bottle to be inspected; an observation unit for observing the illumination light transmitted through the sidewall of the bottle by an elongate observation portion which is movable in synchronization with the elongate illumination portion, so as to observe an image of the entire sidewall of the bottle formed by the transmitted light; and a judge unit for judging whether there is a defect on the sidewall of the bottle, based on the transmitted light image of the bottle observed by the observation unit.

In the method and the device for inspecting the sidewall of a bottle according to this invention, an elongate illumination portion is moved to irradiate illumination light to the sidewall of the bottle to be inspected, an elongate observation portion moved synchronously with the elongate illumination portion to observe the illumination light transmitted through the sidewall of the bottle, and based on an image of the transmitted light, the presence of defects is judged. Light blocking defects and refractional defects on the sidewall of the bottle can be detected with high precision.

DETAILED DESCRIPTION OF THE INVENTION

Figure 1:
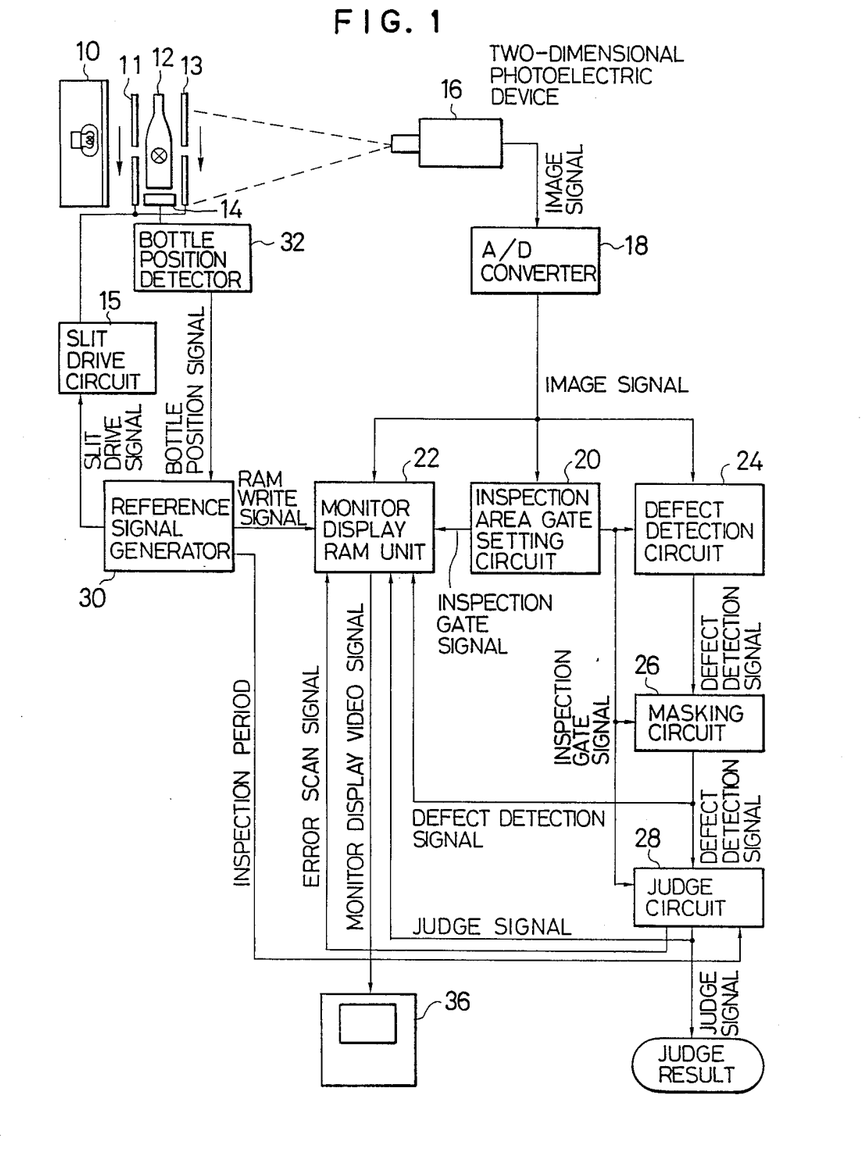
FIG. 1 is a block diagram of the device for inspecting the sidewall of a bottle according to a first embodiment of this invention.

A device for inspecting the sidewall of a bottle according to a first embodiment of this invention is shown in FIG. 1. In this embodiment, a bottle 12 to be inspected is rotated on a rotary mount 14. The bottle 12 is illuminated by diffused light from a diffused light source 10. The bottle 12 is illuminated with a part of the diffused light passing a slit plate 11 positioned between the diffused light source 10 and the bottle 12. Accordingly, a horizontally elongate beam of the part of the diffused light which has passed the slit 11a illuminates the bottle 12.

The light transmitted through the sidewall of the bottle 12 is incident on a two dimensional photoelectric device 16 through a slit plate 13. The two dimensional photoelectric device 16 comprises an area CCD 16a for converting an image of the transmitted light into an electric analog signal, and an optical system 16b for forming the transmitted light image on the area CCD 16a. The two dimensional photoelectric device 16, which detects the transmitted light through the slit plate 13, detects only an elongate portion of the whole transmitted light image of the bottle 12.

Figure 2:
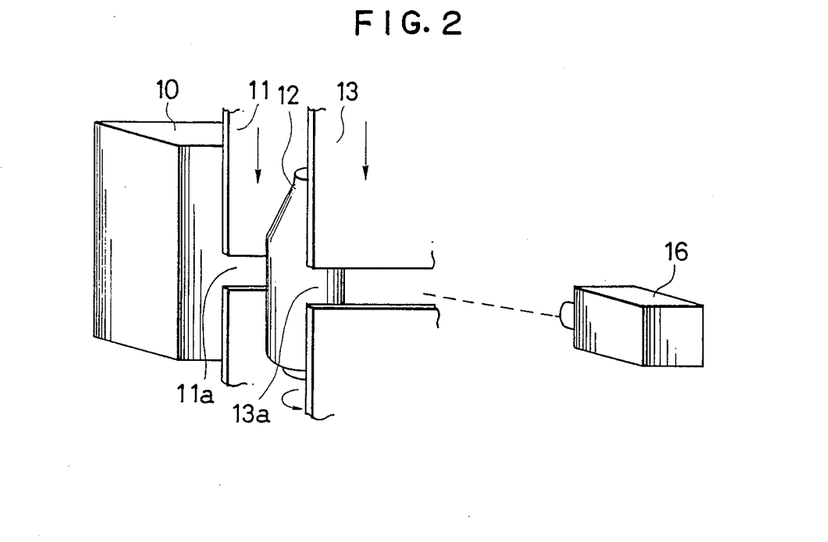
FIG. 2 is a perspective view of an inspection optical system of the device of FIG. 1.
Figure 3:
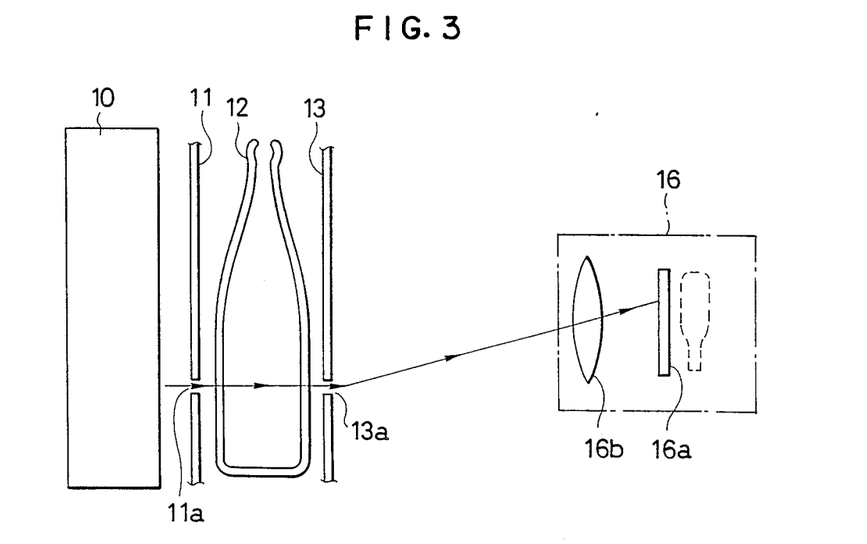
FIG. 3 is a portional view of an inspection optical system of the device of FIG. 1.

The slit plates 11 and 13 are moved up and down by a slit driving circuit 15. In this embodiment, as shown in FIGS. 2 and 3, the slit plates 11 and 13 are driven synchronously so that the slit 11a of the slit plate 11 and the slit 13a of the slit plate 13 are constantly on the same level. Accordingly, as shown in FIG. 3, only a part of the illumination diffused light which has passed the slit 11a passes the bottle 12 passes the slit 13a on the opposite side to form an image of the transmitted light on the area CCD 16 of the two dimensional photoelectric device 16.

Figure 4A:
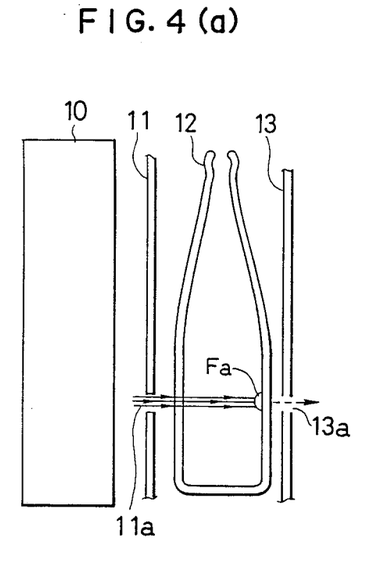
FIG. 4 is an explanatory view of the inspection principle of the device of FIG. 1.

As shown in FIG. 4(a), if a light blocking defect Fa is on the sidewall of the bottle 12, the light which has passed the slit 11a is blocked by the defect Fa, failing to pass the slit 13a consequently without reaching the area CCD 16a of the two dimensional photoelectric device 16. Accordingly the light blocking defect Fa is detected as a shadow on the transmitted light image.

Figure 4B:
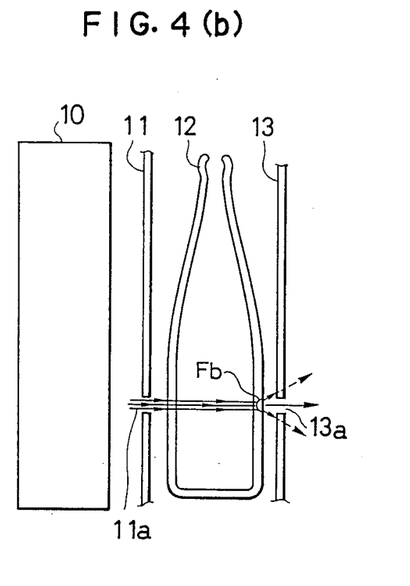

As shown in FIG. 4(b), if a refractional defect Fb is In the bottle 12, the light which has passed the slit 11a is refracted by the defect Fb to be deflected from the direction of straight advance. Most of the light fails to pass the slit 13a consequently without reaching the area CCD 16a of the two dimensional photoelectric device 16. The refractional defect Fb is also detected as a shadow on the transmitted light image.

The slits 11a and 18a are formed in the direction orthogonal to the longitudinal joint of the bottle 12. Accordingly it does not happen that the joint is erroneously detected as a refractional defect.

Figure 5:
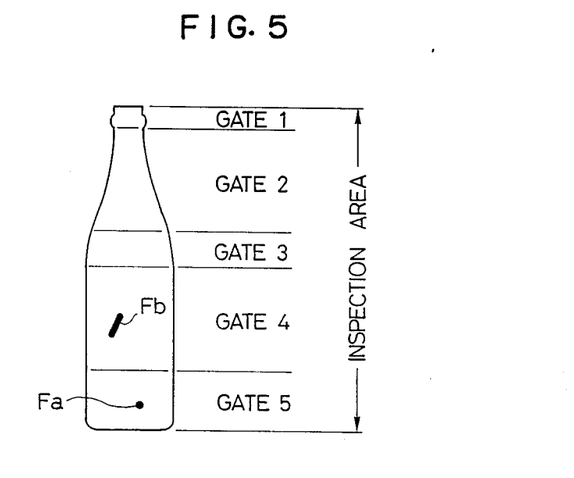
FIG. 5 is a view of an inspection area and inspection gates of the device of FIG. 1.

The slits 11a and 13b of the slit plates 11 and 13 are moved at least once or more times from the mouth of the bottle 12 to the bottom thereof, so that a transmitted light image of the entire bottle 12 is formed on the area CCD 16a of the two dimensional photoelectric device 16. Specifically, as the slit 11a is moved upward, the elongate illumination portion provided by the slit 11a moves upward along the bottle 12, and synchronously with the upward movement of the slit 11a, the slit 13a is moved upward. On the area CCD 16a are sequentially formed elongate images of the transmitted lights through the slit 13a moved upward. Finally an entire transmitted light image of the bottle 12 is formed on the area CCD 16a as shown in FIG. 5. In the transmitted light image of FIG. 6, Fa represents a light blocking defect, and Fb denotes a refractional defect.

An A/D converter 18 converts an analog image signal into a required bit digital image signal. This digital image signal is supplied to an inspection area gate setting circuit 2, a monitor display RAM unit 22 and a defect detection circuit 24.

The inspection area gate setting circuit 20 sets, based on the transmitted light image shown in FIG. 5, an inspection area for the defect detection circuit 24 to inspect, which will be explained below. An inspection area is defined by the top and bottom edges of the bottle 12, and the inspection area is divided into a plurality of inspection gates in accordance with a contour of the bottle 12. In FIG. 5, the inspection area is set for the entire bottle 12, and the inspection area is divided into five inspection gates 1, 2, 3, 4, 5 in accordance with the contour of the bottle 12. The inspection area gate setting circuit 20 supplies to the monitor display RAM unit 22, the defect detection circuit 24 and a masking circuit 26 and a judge circuit 28 an inspection gate signal indicating which inspection gate of an inspection are a current read line on the area CCD 16a correspond to.

But, in the case there the contour of the bottle 12 is not definite, it is possible to preset an inspection area and inspection gates 1, 2, 3, 4, 5 by the inspection area ate setting circuit 20.

The defect detection circuit 2 compares in brightness plural sets of points each spaced horizontally or vertically from one another by a certain distance so as to detect defects.

The defect detecting method includes a two point defect detecting system, in which brightness is compared between two points, and a three point defect detecting system in which brightness is compared among three points. FIG. 6 explains the two point defect detecting system, and FIG. 7 explains the three point defect detecting system.

In the two point defect detecting system, when the following formula $$|QA-QB| \geq (\text{constant A})$$

in which brightnesses at two points A and B are represented by QA and QB respectively is satisfied, there are defects.

Figure 6A:
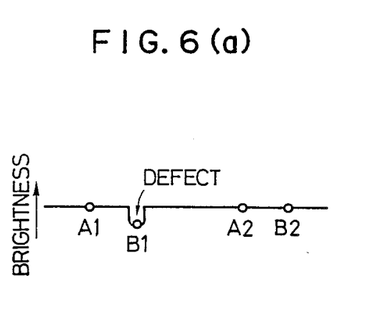
FIG. 6 is an explanatory view of a to point defect detecting system of FIG. 1.
Figure 6B:
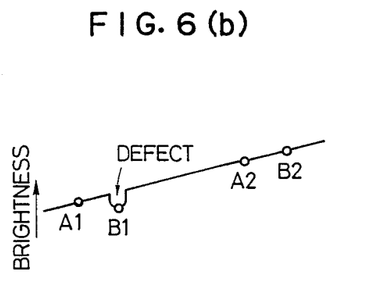

In the case of FIG. 6, defects can be detected by the following formula $$|QA1-QB1| \geq (\text{constant A})$$

$$|QA2-QB2| \geq (\text{constant A})$$

in which brightnesses at points A1 and B1, and A2 and B2 on one scanning line are represented respectively by QA1, QB1, QA2, QB2. A constant A is preset in accordance with types, etc. of the bottle 12. As shown in FIG. 6(a), when a transmitted light image has even brightness along a scanning line, $$QA1-QB1 \geq A$$

$$QA2-QB2=0$$

are satisfied, and it is found that the point B1 is a defect. This two point defect detecting system is effective for the case of even brightness. In the case of uneven brightness along a scanning line as shown in FIG. 6(b), the following formulas $$|QA1-QB1|<A$$

$$|QA2-QB2|<A$$

are given There is a risk that the defect at the point B1 will be missed.

But the three point defect detecting system enables defects to be detected without failure even in the case of uneven brightness along a scanning line as shown in FIG. 6(b). In the three point defect detecting system the following formula $$|QB-\{(QA+QC)/2\}| \geq (\text{constant B})$$

in which brightness at three points A, B, and C are represented by QA, QB and QC is used to detect defects. A constant B is preset in accordance with types, etc. of the bottle 12.

Figure 7A:
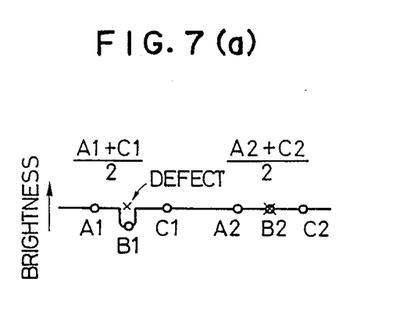
FIG. 7 is an explanatory view of a three point defect detecting system of the device of FIG. 1.
Figure 7B:
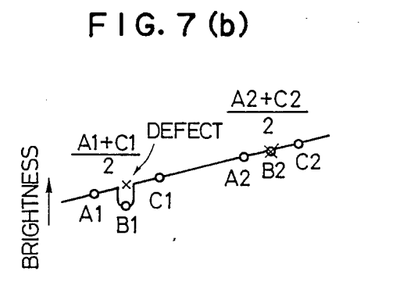

In the case of FIG. 7, defects are detected using the following formulas $$|QB1-\{(QA1+QC1)/2\}|\geqq(\text{constant B})$$

$$|QB2-\{(QA2+QC2)/2\}|\geqq(\text{constant B})$$

in which brightnesses at points A1, B1, C1, A2, B2, C2 on a scanning line of the area CCD 16a are represented by QA1, QB1, QC1, QA2, QB2, QC2. The brightnesses compared with those at intermediate points B1 and B2 are an arithmetic average of the brightnesses of points A1 and C1 on both sides of the intermediate point B1 and that of the brightnesses of points A2 and C2 on both sides of the intermediate point B2. The three point defect detecting system enables the defect B1 to be detected correctly both in the case of even brightness as in FIG. 7 and in the case of uneven brightness as in FIG. 7(b).

Figure 8:
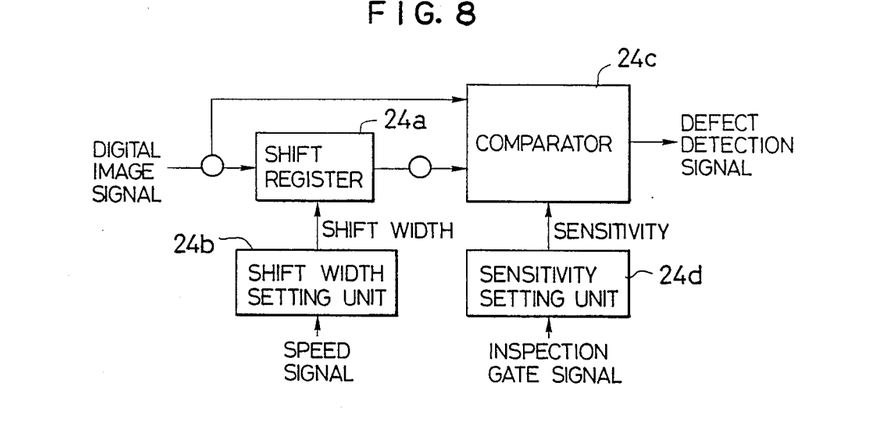
FIG. 8 is a block diagram of a defect detecting circuit for performing the two point defect detecting system.

FIG. 8 shows an example of the defect detection circuit 24 of the to point defect detecting system. The distance between two points is determined by a shift width of a shift register 24a to which is sequentially inputted a digital image signal. The shift width is determined by a shift width setting unit 24b. A comparator 24c compares a currently inputted digital image signal with an output signal of the shift register 24a which is a preceding signal by a shift width so as to judge whether or not the absolute value of a difference between the to is larger than a sensitivity (i.e., a constant A) set by the sensitivity setting unit 24d. The constant A may vary for the inspection gates. The sensitivity setting unit 24d outputs a suitable constant A based on an input inspection gate signal to the comparator 24c.

Figure 9:
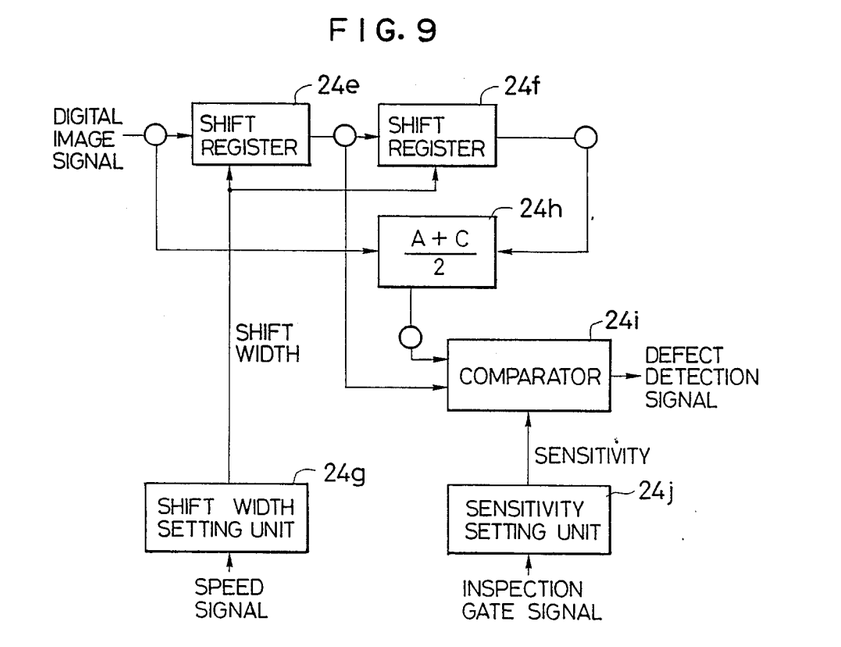
FIG. 9 is a block diagram of a defect detecting circuit for performing the three point defect detecting system.

FIG. 9 shows an example of the defect detection circuit 24 of the three point defect detecting system. The distance between one of the three points and an adjacent one is determined by shift widths of a shift registers 24e, 24f to which are sequentially supplied digital image signals. In this example, the two shift registers 24e, 24f have the same shift width. A computing circuit 24h computes an arithmetic average of a current input digital image signal and a digital image signal outputted from the shift register 24f. A comparator 24i compares an average brightness computed by the computing circuit 24h with a digital image signal from the shift register 24e to judge whether or not the absolute value of a difference between the two is larger than a sensitivity (i.e., a constant B) set by a sensitivity setting unit 24j to output a defect detecting signal. The constant B varies for the inspection gates. The sensitivity setting unit 24j outputs to the comparator 24i a suitable constant B based on an input inspection gate signal.

The brightness comparison between to points and among three points of FIGS. 8 and 9 are performed both vertically and horizontally of the area CCD 16a, i.e., vertically and horizontally of the bottle 12.

A defect detection signal outputted from the defect detection circuit 24 is subjected to a masking process by a masking circuit 26. When the sensitivity of the defect detection circuit 24 is increased to avoid errors in the defect detection, a part which is not a defect is falsely detected as a defect. The masking process is for removing such false defect detection signal. At a real defect detection signals are continuously generated in accordance with a size of the defect, and an the remaining normal part, defect detection signals are separately generated. The masking process eliminates as a false defect detection signal an isolated defect detection signal and continuous defect detection signals only below a set value.

A judge circuit 28 judges whether or not a defect is present, based on defect detection signals which have been masking processed. For example, a number of the defect detection signals are counted for each scan, and when the counted value exceeds a set value, the scan is judged an error scan (a defect scan line). The judge circuit 28 further counts a number of continuous error scans, and when the counter value exceeds a set value, the bottle 12 is judged a defective bottle. A resultant judge signal is outputted to a conveying line (not shown), and in accordance with the judge signal, the conveying system ejects the defective bottle.

A reference signal generator 30 generates a slit driving signal, an inspection period signal and a RAM write signal, based on a bottle position signal from a bottle position detector 32.

The slit driving signal is for moving the slit plates 11, 13 from the top to the bottom in accordance with a scan of the CCD 16a during one rotation of the bottle 12 and is supplied to the slit drive circuit 15. The slit drive circuit 15 moves the slit plates 11, 13, based on a slit driving signal. The inspection period signal is for indicating an inspection period in which the slit plates 11, 13 are moving and is supplied to the judge circuit 28. The RAM write signal is for indicating a timing for a digital image signal to be written in the monitor display RAM unit 22.

The reference signal generator 30 comprises a LA (Programmable Logic Array) to generate the slit driving signal, the inspection period signal the RAM write signal That is, a bottle position signal is set as an address, and a slit driving signal, an inspection period signal and a RAM rite signal are written in the address. When a bottle position signal is inputted as an address signal, a suitable slit driving signal, inspection period signal and RAM write signal are outputted.

An inspection period signal from the reference signal generator 30 is outputted to the judge circuit 28. The judge circuit 28 takes as effective signals only defect detection signals inputted thereto in a period in which the inspection period signal is at a high level and judges whether or not the bottle 12 is defective. It is also possible that the inspection period signal is supplied to the inspection area gate setting circuit 20, the defect detection circuit 24 or the masking circuit 26, and only the defect detection signals inputted thereto in a period in which the inspection period signal is at high level are taken as effective signals.

A RAM write signal from the reference signal generator 30 is supplied to the monitor display RAM unit 22. Based on &he RAM write signal, a digital image signal from the A/D converter is written in the monitor display RAM unit 22. The monitor display RAM unit 22 has been supplied with, in addition to the RAM write signal, a defect detection signal from &he masking circuit 26, an error scan signal and a judge result signal from the judge circuit 28, and a inspection gate signal from the inspection area gate setting circuit 20. Based on the defect detection signal and the error scan signal, defects and error scans are written in the monitor display RAM circuit 22. Based on the inspection gate signal, an inspection gate is displayed on a monitor 36.

The monitor display RAM unit 22 has two frame memories. Alternately in the to frame memories is stored a digital image signal of the bottle 12 under inspection, and a digital image signal of a bottle previously inspected. Normally digital image signals of the bottle 12 under inspection are sequentially displayed on the monitor. When a judge signal indicating the bottle 12 is defective, the frame memory storing the digital image signal of the defective bottle is displayed on the monitor 36 for further observation of the defect.

As described above, this first embodiment permits not only light blocking defects but also refractional defects to be detected with high sensitivity.

Figure 10:
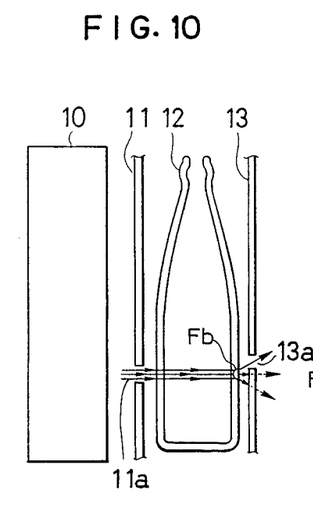
FIG. 10 is an explanatory view of the inspection principle of a modification of the first embodiment.
Figures 11A, 11B:
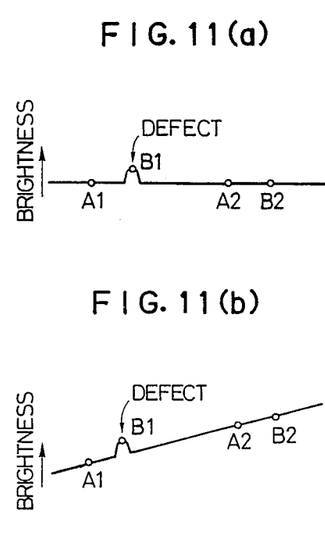
FIG. 11 is an explanatory view of the two point defect detecting system for the modification of FIG. 10.
Figures 12A, 12B:
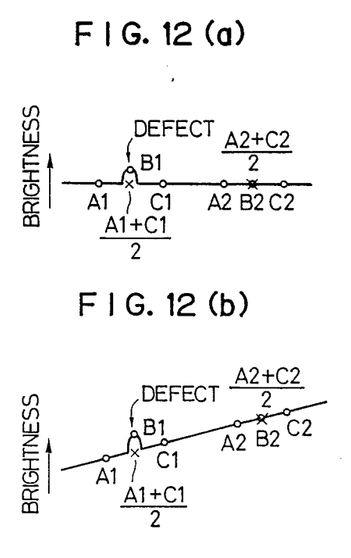
FIG. 12 is an explanatory vie of the three point defect detecting system for the modification of FIG. 10.
Figure 13:
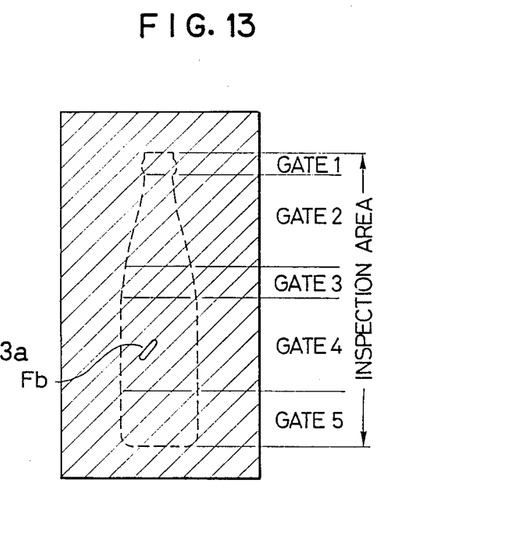
FIG. 13 is a view exemplifying the transmitted light image in the modification of FIG. 10.

In this first embodiment, the slit 11a of the slit plate 11 and the slit 13a of the slit plate 13 are positioned on the same level. But as shown in a modification of FIG. 10, the slit 11a and the slit 13a may be offset by a predetermined distance, and it is preferable that the slit 13a is located at a position where the illumination light which has advanced straight through the slit 11a is nearly blocked by the slit plate 13. The illumination light through the slit 11a which passes a part without any defect is blocked by the slit plate 13. When a refractional defect Fb is present in the bottle 12, however, as shown in FIG. 10, the light which has passed the slit 11a is deflected to pass the slit 13a. Accordingly, as shown in FIGS. 11 and 12, a defect appears as a brighter defect point B1 than the other normal points. A refractional defect, as shown in FIG. 13, appears as a refractional defect Fb which is a brighter area in a transmitted light image. This modification is not able to detect the light blocking defect Fa.

This modification can use the to point defect detecting system (FIG. 11) and the three point defect detecting system (FIG. 12) as the first embodiment does. A difference of this modification from the first embodiment is that the defect point is brighter in the former.

Figure 14:
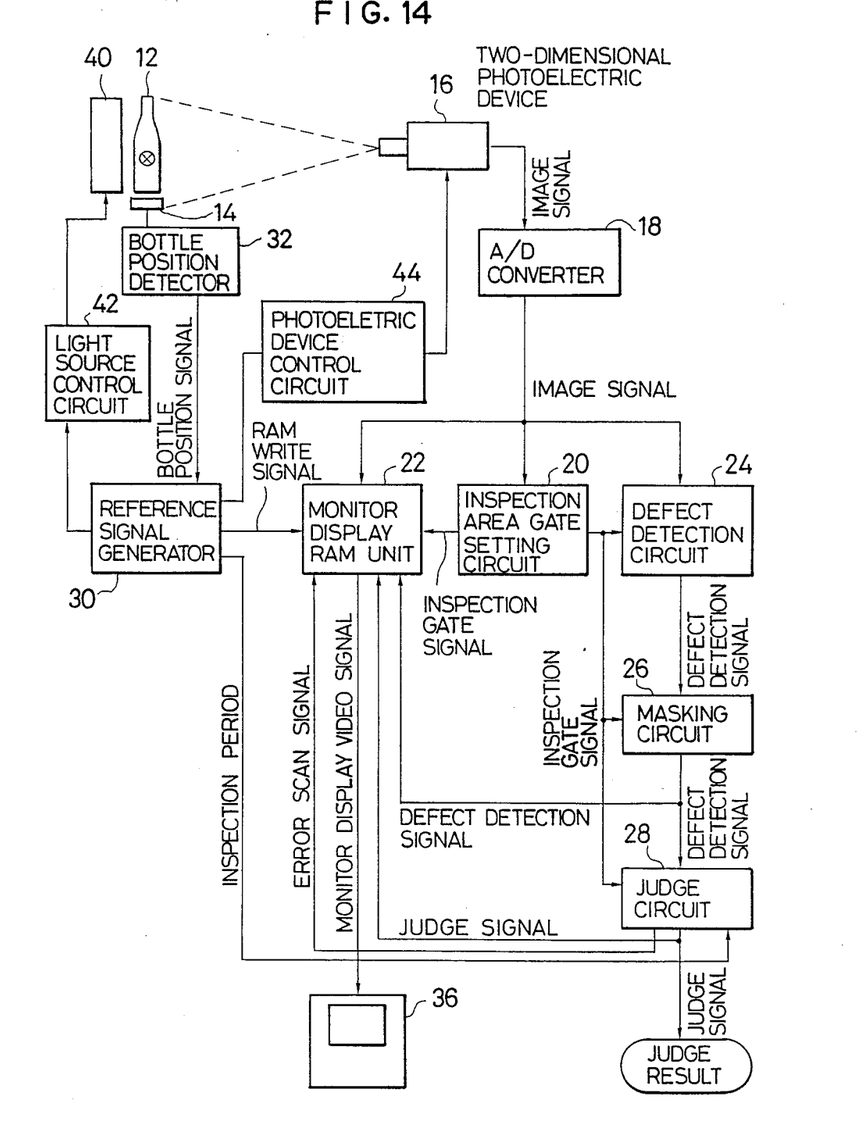
FIG. 14 is a block diagram of the device for inspecting the sidewall of a bottle according to a second embodiment of this invention.

FIG. 14 shows the device for inspecting the sidewall of a bottle according to a second embodiment of this invention. Common members have common reference numerals, and their explanations will not be repeated. The second embodiment is characterized in that mechanically operative members, such as the slit plates 11, 13, are not included.

Figure 15:
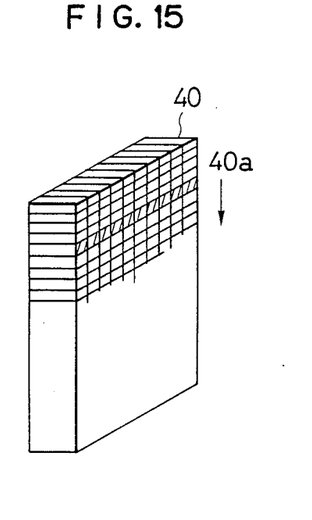
FIG. 15 is a perspective view of a light source of the device of FIG. 14.

In this embodiment, as shown in FIG. 15, a light source 40 is provided in place of the diffused light source 10 and the slit plate 11. The light source 40 comprises a number of light emitting diodes 40a arranged in a matrix. In place of moving the slit plate 11, the light emission of each light emitting diode 40a is controlled by a light source control unit 42. Specifically, the light emitting diodes 40a are actuated downwardly subsequently one row after another, which provides the function of moving the slit plate 11 in the first embodiment. In FIG. 13 a fourth row of the light emitting diodes is actuated.

Figure 16:
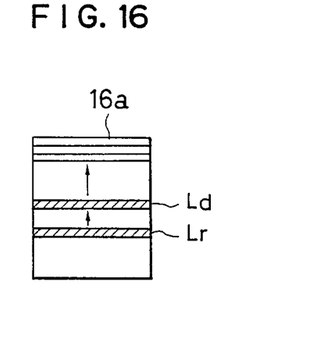
FIGS. 16 and 17 are explanatory views of methods for controlling an area CCD of the device of FIG. 14.
Figure 17:
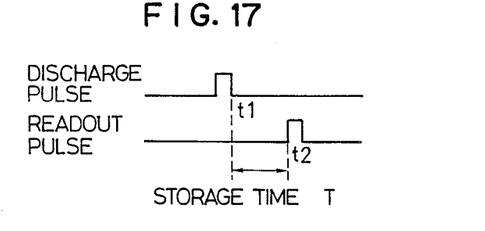

In this embodiment, instead of the slit 13, the discharge and the readout of the area CCD 16a of the to dimensional photoelectric device 16 is controlled by a photoelectric device control circuit 44. Specifically, as shown in FIG. 16, a discharge control line Ld is moved upward so as to discharge a stored electric charge, and a readout control line Lr which controls a stored electric charge to be read is moved upward following the discharge control line Ld. FIG. 17 shows the control timing for one line. When a discharge pulse is generated at a time t1, the electric charge which has been stored up to the time is discharged. An electric charge is stored in accordance with a next incident light. When a readout pulse is generated at a time t2 after a storage time T, the electric charge which has been stored in the storage time T is read out as a signal. An interval between a discharge control line Ld and a readout control line Lr determined by a storage time T corresponds to a gap of the slit 13a.

Figure 18:
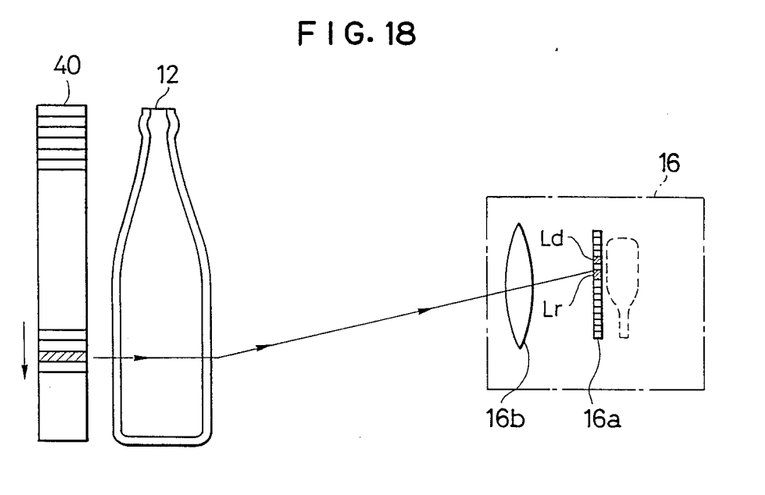
FIG. 18 is a view of a detection optical system of the device of FIG. 14.

The reference signal generator 30 supplies a control signal to the light source control circuit 42 and to the photoelectric device control circuit 44 so as to synchronize a row of light emitting diodes to be actuated, and a discharge control lined Ld and a readout control line Lr of the area CCD 16a with each other. For example, as shown in FIG. 18, their control is made so that a portion of a transmitted light image of the bottle 12 illuminated with an actuated row of light emitting diodes is formed at the middle between a discharge control line Ld and a readout control line Lr of the area CCD 16a. This is equivalent to FIG. 3 of the first embodiment (where the slit 11a and the slit 13a are aligned). In order to obtain the same function of FIG. 10 (where the slit 11a and the slit 13a are offset), an image forming position of an actuated row of light emitting diodes, and a light storing region between a discharge control line Ld and a readout control line Lr are offset by a predetermined distance.

This embodiment, which includes no mechanically operative members, facilitates easy precise positioning and decreases occurrences of failures.

In the above described second embodiment, the light source 40 is provided by light emitting diodes arranged in a matrix, but, as long as elongate illumination portion can be switched, the light source 40 may be any means. To give an example, light is led by optical fibers bundled in a matrix to provide elongate illumination portion or a laser beam is caused to scan and switch elongate illumination portions.

This invention is not limited to the above described embodiments but includes various modifications. For example, in the above described embodiment, the inspection is made on &he bottle 12 rotated, staying at a fixed position, but it is possible inspect the bottle 12 rotated on continuous move with additions of a vibratory lens or mirror.

The defect detection system is not limited to the above described ones but includes various modifications. To give an example, it may be possible that when the following formulas $$QA/QB \geq \text{(constant C)}$$

$$QA/QB \geq 1/\text{(constant C)}$$

wherein brightnesses at two points to be compared are represented by QA and QB are satisfied, there is a defect. It may be also possible that one of the following formulas $$QB/\{(QA+QC)/2\} \geq \text{(constant D)}$$

$$QB/\{(QA+QC)/2\} \geq 1/\text{(constant D)}$$

wherein brightnesses at three points to be compared are indicated by QA, QB and QC are satisfied, there is a defect. Constants C and D are numbers larger than 1.

Furthermore, the first and the second embodiments may be combined. Specifically, the diffused light source and the slit plate of the first embodiment are used as the illumination unit, and as the observation unit the area CCD may be controlled as in the second embodiment. Conversely, the light source comprising light emitting diodes in the second embodiment may be used as the illumination unit, and as the observation unit, the slit plate as in the first embodiment may be used.

The elongate illumination portion and the elongate observation portions are really horizontal to the bottle in the above described embodiment but may be positioned in a direction other than the really horizontal direction. The elongate illumination portion and the elongate observation portion are not necessary straight but may be curved.

The bottle may be glass or plastic. This invention is applicable to the inspection on the sides of glass containers.

What is claimed is:

1. A method for inspecting the sidewall of a bottle comprising the steps of
    moving an elongate illumination portion to irradiate illumination light to the entire sidewall of the bottle to be inspected;
    observing the illumination light transmitted through the sidewall of the bottle by an elongate observation portion moved synchronously with the illumination portion to observe an image of the entire sidewall formed by &he transmitted light; and
    judging whether there is a defect on the sidewall of the bottle, based on the transmitted light image.

2. A method for inspecting the sidewall of a bottle according to claim 1, wherein:
    the elongate illumination portion and the elongate observation portion are synchronously moved so that the illumination light through the elongate illumination portion passes the sidewall to reach the elongate observation portion; and
    when the elongate observation portion observes none of the illumination light through the elongate illumination portion, the judgement is that a light blocking defect is on the sidewall of the bottle.

3. A method for inspecting the sidewall of a bottle according to claim 1, wherein:
    the elongate illumination portion and the elongate observation portion are synchronously moved with each other, offset from each other by a predetermined distance so that none of the illumination light through the elongate illumination portion pass the sidewall to reach the elongate observation portion; and
    when the illumination light through the elongate illumination portion is observed by the elongate observation portion, the judgement is that there is a refractional defect is on the sidewall of the bottle.

4. A device for inspecting the sidewall of a bottle comprising:
    an illumination unit for moving an elongate illumination portion to irradiate illumination light to the entire sidewall of the bottle to be inspected;
    an observation unit for observing the illumination light transmitted through the sidewall of the bottle by an elongate observation portion which is movable in synchronization with the elongate illumination portion, so as to observe an image of the entire sidewall of the bottle formed by the transmitted light; and
    a judge unit for judging whether there is a defect on the sidewall of the bottle, based on the transmitted light image of the bottle observed by the observation unit.

5. A device for inspecting the sidewall of a bottle according to claim 4, wherein:
    the elongate illumination portion and the elongate observation portion are synchronously moved so that the illumination light through the elongate illumination portion passes the sidewall to reach the elongate observation portion; and
    the judge unit judges that, when the elongate observation portion observes none of the illumination light through the elongate illumination portion, a light blocking defect is on the sidewall of the bottle.

6. A device for inspecting the sidewall of a bottle according to claim 4, wherein:
    the elongate illumination portion and the elongate observation portion are moved in synchronization with each other, offset from each other by a predetermined distance so that none of the illumination light through the elongate illumination portion pass the sidewall to reach the elongate observation portion; and
    the judge unit judges that, when the illumination light through the elongate illumination portion is observed by the elongate observation portion, the judgement is that there is a refractional defect is on the sidewall of the bottle.

7. A device for inspecting the sidewall of a bottle according to claims 4, wherein:
    the illumination unit comprising:
    a light source for emitting illumination light;
    an illumination slit for allowing an elongate part of the illumination light from the light source to pass; and
    means for moving the illumination slit;
    the observation unit comprising:
    an observation slit for allowing the illumination light transmitted through the bottle to pass;
    means for moving the observation slit; and
    light detecting means for detecting the transmitted light which has passed the observation slit.

8. A device for inspecting the sidewall of a bottle according to claims 5, wherein:
    the illumination unit comprising:
    a light source for emitting illumination light;
    an illumination slit for allowing an elongate part of the illumination light from the light source to pass; and
    means for moving the illumination slit;
    the observation unit comprising:
    an observation slit for allowing the illumination light transmitted through the bottle to pass;
    means for moving the observation slit; and
    light detecting means for detecting the transmitted light which has passed the observation slit.

9. A device for inspecting &he sidewall of a bottle according to claims 6, wherein:
    the illumination unit comprising:
    a light source for emitting illumination light;
    an illumination slit for allowing an elongate part of the illumination light from the light source to pass; and
    means for moving the illumination slit;
    the observation unit comprising:
    an observation slit for allowing the illumination light transmitted through the bottle to pass;
    means for moving the observation slit; and
    light detecting means for detecting the transmitted light which has passed the observation slit.

10. A device for inspecting the sidewall of a bottle according to claims 4, wherein:

the illumination unit comprising:
a plurality of elongate light emitting portions; and
control means for making said plurality of elongate light emitting portions operative to emit the illumination light in a predetermined sequential order;
the observation unit comprising:
a plurality of light detecting portions; and
control means for making said plurality of light detecting portions operative to detect the transmitted light in a predetermined sequential order.

11. A device for inspecting the sidewall of a bottle according to claims 5, wherein:
the illumination unit comprising:
a plurality of elongate light emitting portions; and
control means for making said plurality of elongate light emitting portions operative to emit the illumination light in a predetermined sequential order;
the observation unit comprising:
a plurality of light detecting portions; and
control means for making said plurality of light detecting portions operative to detect the transmitted light in a predetermined sequential order.

12. A device for inspecting the sidewall of a bottle according to claims 6, wherein:
the illumination unit comprising:
a plurality of elongate light emitting portions; and
control means for making said plurality of elongate light emitting portions operative to emit the illumination light in a predetermined sequential order;
the observation unit comprising:
a plurality of light detecting portions; and
control means for making said plurality of light detecting portions operative to detect the transmitted light in a predetermined sequential order.

* * * * *